United States Patent
Akiyama et al.

(10) Patent No.: US 6,881,970 B2
(45) Date of Patent: *Apr. 19, 2005

(54) CHARGED PARTICLE BEAM IRRADIATION EQUIPMENT AND CONTROL METHOD THEREOF

(75) Inventors: Hiroshi Akiyama, Hitachioota (JP); Hiroshi Kubo, Hitachi (JP); Kazuo Hiramoto, Hitachioota (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/716,472

(22) Filed: Nov. 20, 2003

(65) Prior Publication Data

US 2004/0069959 A1 Apr. 15, 2004

Related U.S. Application Data

(63) Continuation of application No. 09/623,040, filed on Aug. 25, 2000.

(30) Foreign Application Priority Data

Sep. 27, 1999 (WO) .............................. PCT/JP99/05250

(51) Int. Cl.$^7$ .............................. G21K 5/00; H01J 7/28; G01M 23/00
(52) U.S. Cl. ................. 250/492.3; 250/492.1; 250/492.21; 250/492.22; 250/396 R; 250/397; 250/398; 250/306; 250/307; 250/309
(58) Field of Search .................. 250/492.1–492.3, 250/396–398, 306–309; 315/162–174

(56) References Cited

U.S. PATENT DOCUMENTS 3,893,075 A 7/1975 Orban et al.
3,937,997 A 2/1976 Barrett
3,950,651 A 4/1976 Flocee
4,368,409 A 1/1983 Sivanesan et al.
4,421,988 A 12/1983 Robertson et al.
4,551,655 A 11/1985 Timmermans et al.
4,812,716 A 3/1989 Miyama et al.
4,939,413 A 7/1990 Tomli et al.
4,961,056 A 10/1990 Yu
4,992,746 A 2/1991 Martin (Continued)

FOREIGN PATENT DOCUMENTS

| EP | 779 081 | 6/1997 |
|---|---|---|
| JP | 6-112000 | 4/1994 |
| JP | 8-88972 | 4/1996 |
| JP | 9-223600 | 8/1997 |

*Primary Examiner*—John R. Lee
*Assistant Examiner*—Bernard E. Souw
(74) *Attorney, Agent, or Firm*—Mattingly, Stanger, Malur & Brundidge, P.C.

(57) ABSTRACT

A power supply for applying a voltage to a scanning electromagnet for deflecting a charged particle beam has a first power supply unit having no filter and a second power supply unit having a filter. When an irradiation position of the charged particle beam in an irradiation object is moved, the first power supply unit, namely a power supply unit having no filter, is used to apply the voltage to the scanning electromagnet, so that an exciting current flowing in the scanning electromagnet can be changed in a short time. Further, when the irradiation position of the charged particle beam is maintained, the second power supply is used to apply a voltage whose pulsating component was removed to the scanning electromagnet, so that the exciting current flowing in the scanning electromagnet can be controlled precisely. Consequently, the charged particle beam can be applied uniformly to the irradiation object and an irradiation time of the charged particle beam to the irradiation object can be curtailed.

8 Claims, 7 Drawing Sheets

U.S. PATENT DOCUMENTS

| | | | |
|---|---|---|---|
| 5,063,294 A | | 11/1991 | Kawata et al. |
| 5,073,913 A | | 12/1991 | Martin |
| 5,349,515 A | * 9/1994 | Megeid | 363/21.11 |
| 5,349,516 A | * 9/1994 | Megeid | 363/21.08 |
| 5,351,177 A | * 9/1994 | Megeid | 363/21.09 |
| 5,363,008 A | | 11/1994 | Hiramoto et al. |
| 5,557,105 A | | 9/1996 | Honjo et al. |
| 5,786,669 A | | 7/1998 | Kobori et al. |
| 5,969,367 A | | 10/1999 | Hiramoto et al. |
| 6,066,849 A | | 5/2000 | Masnaghetti et al. |
| 6,316,776 B1 | | 11/2001 | Hiramoto et al. |
| 6,346,773 B1 | * 2/2002 | Takegami | 315/169.1 |
| 6,410,929 B1 | | 6/2002 | Nakamura et al. |
| 6,472,834 B1 | | 10/2002 | Hiramoto et al. |
| 2002/0014588 A1 | | 2/2002 | Hiramoto et al. |
| 2002/0101959 A1 | | 8/2002 | Kato et al. |
| 2002/0128807 A1 | | 9/2002 | Sakamoto et al. |
| 2003/0057382 A1 | * 3/2003 | Akiyama et al. | 250/492.3 |
| 2004/0069959 A1 | * 4/2004 | Akiyama et al. | 250/492.3 |

\* cited by examiner

CHARGED PARTICLE BEAM IRRADIATION EQUIPMENT AND CONTROL METHOD THEREOF

This application is a continuation application of U.S. Ser. No. 09/623,040, filed Aug. 25, 2000. This application is related to U.S. Ser. No. 10/287,656, filed Nov. 5, 2002.

TECHNICAL FIELD

The present invention relates to a charged particle beam irradiation equipment for irradiating an irradiation object with a charged particle beam, and its control method.

BACKGROUND ART

For a charged particle irradiation equipment for irradiating an irradiation object with a charged particle beam (hereinafter referred to as "beam"), a charged particle beam irradiation equipment for irradiating the affected part of a patient with a beam to perform cancer treatment is known, and in Japanese Published Unexamined Patent Application No. 9-223600 (hereinafter referred to as the "first conventional art"), as an example, described is a charged particle beam irradiation equipment for applying the beam to each irradiation area in order after the affected part was divided into a plurality of the irradiation areas. The charged particle beam irradiation equipment described in the first conventional art controls an irradiation position of the beam with two scanning electromagnets for generating magnetic fields in two mutually orthogonal directions.

In the first conventional art, a configuration of a power supply for supplying power to the scanning electromagnets was not described in detail. However, one may consider a power supply for an electromagnet described in Japanese Published Unexamined Patent Application No. 8-88972 (hereinafter referred to as the "second conventional art") is used for the scanning electromagnets. In this power supply, a filter for removing a pulsating component from its output is provided at the output side of the power supply in order to improve control accuracy of an exciting current flowing in the electromagnet.

As described above, since in the first conventional art, a plurality of irradiation areas are irradiated with the beam in order, the exciting current flowing in the scanning electromagnet increases or decreases in a stepwise manner, for example, as shown in FIG. 5(a). By the way, in the period of time when the current value is constant to the time, the irradiation position of the beam is kept fixed; in the period of time when the current value is changing to the time, the irradiation position is being changed over.

Referring to the period when the current value is changing to the time illustrated in FIG. 5(a), in other words, the period required for the irradiation position of the beam to be changed over, shorter is generally better. Because, as described in the first conventional art, if the irradiation of the beam is being stopped when the irradiation position of the beam is changed over, a period when the position of the beam irradiation is changed becomes dead time. If the dead time is longer, the treatment time will also be longer, causing a patient to be in burden and inconvenience. The time required for the beam irradiation position to be changed over, thus, must be as short as possible. On the contrary, if the beam irradiation is performed even when the irradiation position of the beam is being changed over, the irradiation dose applied in the period of time when the irradiation position of the beam is being changed over must be also considered to figure out the total dose at the affected part, and therefore it becomes difficult to make the irradiation dose at the affected part uniform. To circumvent this, the time necessary for the beam irradiation position to be changed over must be as short as possible so that the irradiation dose applied during the change of the irradiation position become so small as can be ignored. That is, the exciting current flowing in the scanning electromagnet must be changed in a very short time.

However, since the power supply stated in the second conventional art employs a filter for removing the pulsating component, a delay is generated in the output voltage and hence the exciting current flowing in the scanning electromagnet cannot be changed in a short time.

On the contrary, if a power supply without the use of a filter is employed, it may be possible that the exciting current can be changed in a short time, but the control accuracy of the exciting current flowing in the scanning electromagnet deteriorates under the influence of the pulsating component instead. If the control accuracy of the exciting current deteriorates, the irradiation position of the beam may be out of the right place, and therefore the beam cannot be applied uniformly to the affected part.

DISCLOSURE OF THE INVENTION

It is the object of the present invention to provide a charged particle beam irradiation equipment capable of irradiating an irradiation object with a charged particle beam uniformly and reducing the irradiation time of the charged particle beam to the irradiation object, and its control device.

Characteristics of the present invention that achieves the object are in that in the charged particle beam irradiation equipment for irradiating the irradiation object with the charged particle beam comprising a scanning electromagnet for deflecting the charged particle beam and a power supply for applying voltage to the scanning electromagnet, the power supply further comprises a first power supply unit having no filter and a second power supply unit having a filter.

According to the present invention, since the power supply has two power supply units of the first power supply unit having no filter and the second power supply unit having a filter, when the irradiation position of the charged particle beam in the irradiation object is changed over, the first power supply unit having no filter, namely a power supply unit having no delay element, is used to apply the voltage to the scanning electromagnet, so that the exciting current flowing in the scanning electromagnet can be changed in a short time. Therefore, the irradiation position of the charged particle beam can be changed over in a short time, and the irradiation time of the charged particle beam in the irradiation object can be reduced. On the other hand, when the irradiation position of the charged particle beam is maintained, the second power supply unit having the filter is used to apply the voltage whose pulsating components is removed to the scanning electromagnet, consequently the exciting current flowing in the scanning electromagnet can be controlled precisely. Therefore, the charged particle beam irradiation equipment according to the present invention can prevent the irradiation position from moving out of the right position and hence apply the charged particle beam uniformly to the irradiation object. As described above, according to the present invention, the charged particle beam can be applied on the irradiation object uniformly and, the irradiation time of the charged particle beams can be reduced.

BEST MODE FOR CARRYING OUT THE INVENTION

Figure 1:
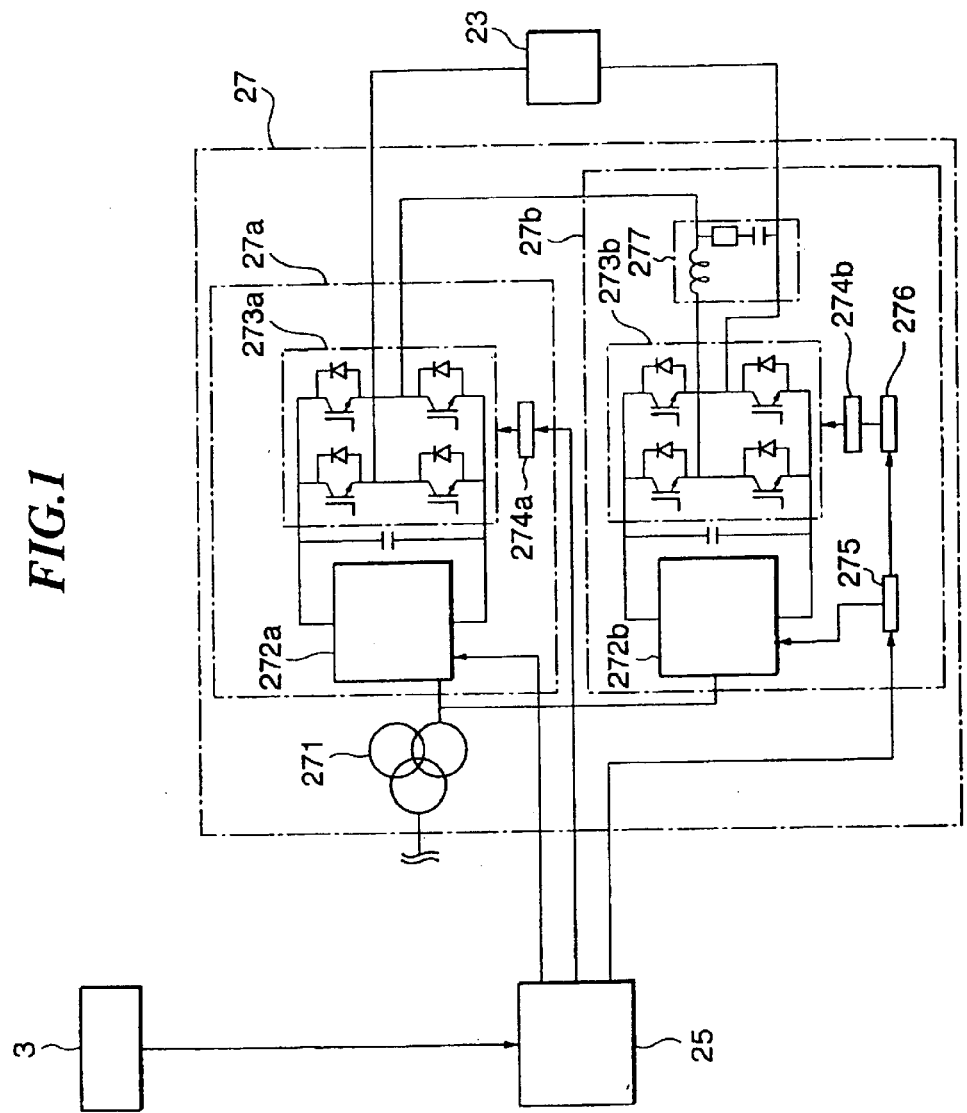
FIG. 1 is a block diagram of a scanning electromagnet power supply in the charged particle beam irradiation equipment that is a preferred embodiment according to the present invention.

Referring to the drawings, the embodiments according to the present invention will be described in detail below.

Embodiment 1

Figure 2:
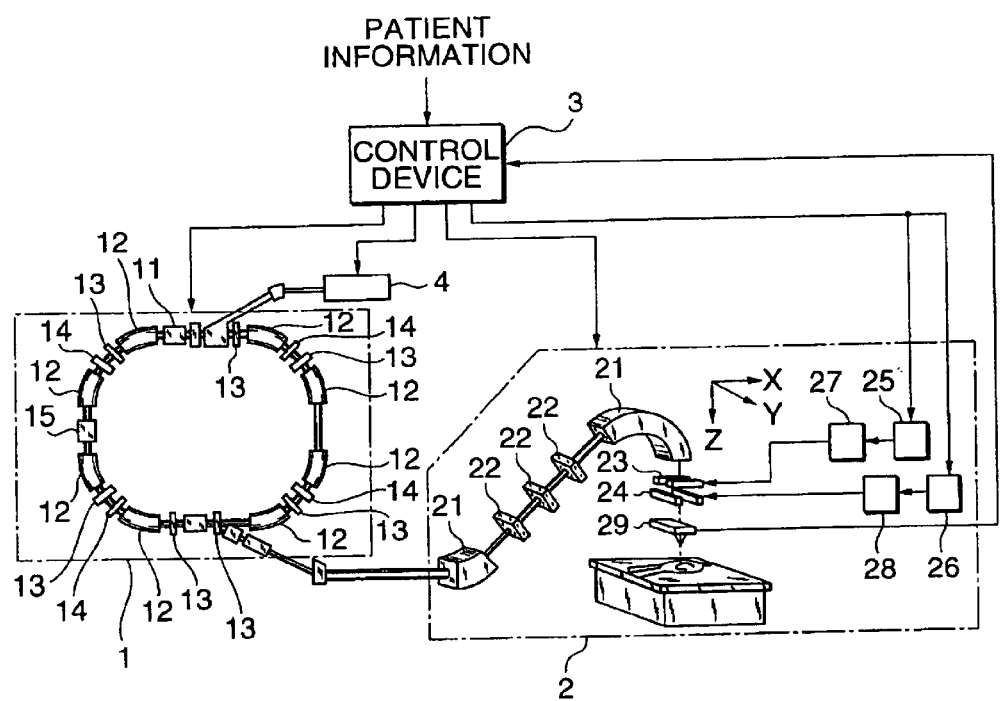
FIG. 2 is a configuration diagram of the charged particle beam irradiation equipment that is a preferred embodiment of the present invention.
Figure 3:
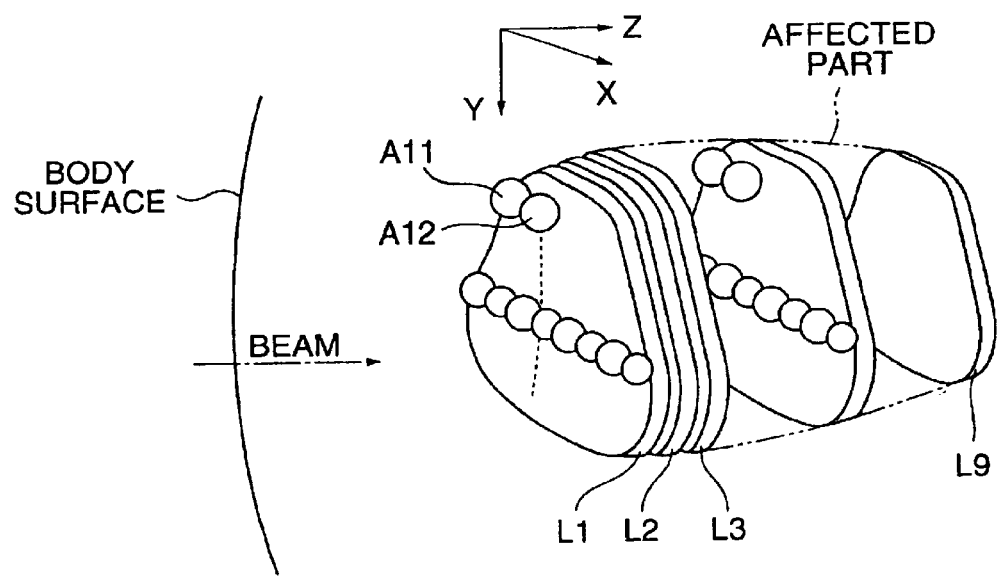
FIG. 3 is an illustration showing a method of beam irradiation to the affected part by the charged particle beam irradiation equipment of FIG. 2.

FIG. 2 shows the charged particle beam irradiation equipment of the preferred embodiment according to the present invention. By the way, the charged particle beam irradiation equipment of FIG. 2 is equipment for performing cancer treatment by applying a charged particle beam accelerated by a synchrotron 1 to the affected part of a cancer patient with a rotational irradiation device 2. Further, the charged particle beam irradiation equipment according to the present embodiment, as shown in FIG. 3, divides the affected part into a plurality of layered areas L1–L9 in a direction of beam propagation, and each layered area is further divided into a plurality of irradiation areas A11, A12, . . . , to each of which the beam is applied.

In the cancer treatment by means of the charged particle beam irradiation equipment of FIG. 2, first patient information such as the depth position of the affected part, the shape of the affected part, irradiation dose to be achieved in the affected part (hereinafter referred to as "irradiation dose"), etc. are entered into a control device 3.The control device 3 determines the energy of the beam emitting from the synchrotron 1, the irradiation position of the beam in the affected part, and the irradiation dose of the beam in the affected part, according to the entered patient information. By the way, the energies of the beam are decided based on respective depth positions of the layered areas L1–L9 from the body surface.

In the present embodiment, the beam is applied in order, to the layered areas, from the layered area L9 that is in the deepest position from the body surface to the layered area L1 that is in the most shallow position. The procedure will be described below.

First, the control device 3 outputs a beam emission command to a preaccelerator 4.Once the beam emission command is entered into the preaccelerator 4, it emits a beam. The beam emitted from the preaccelerator 4 is entered into the synchrotron 1. The control device 3 outputs a beam emission command to the preaccelerator 4, outputs current command values to respective power supplies (not shown in the figure) of deflecting electromagnet 12, a quadruple electromagnet 13, and a hexapole electromagnet 14, and outputs a voltage command value to a power supply (not shown in the figure) of a high-frequency acceleration cavity 15. These current command values and voltage command value are obtained beforehand according to the beam energy. The power supplies to which the current command values are given supply currents to the deflecting electromagnet 12, the quadruple electromagnet 13, and the hexapole electromagnet 14, respectively, and also a voltage is supplied to the high-frequency acceleration cavity 15. By the way, currents supplied to respective magnets are set so as to vary according to acceleration of the beam.

Here, rolls of respective constituent components in the synchrotron 1 will be described. First, the deflecting electromagnet 12 generates a magnetic field in proportion to the supplied current and deflects the beam with the magnetic filed so that the beam goes around the synchrotron 1 on its orbit. The quadruple electromagnet 13 controls a chain of the beam (i.e. a frequency of a period when the beam goes around the synchrotron 1 for one time) by means of the magnetic field according to the supplied current. The high-frequency acceleration cavity 15 applies a high-frequency electric field according to a supplied voltage to the beam and accelerates the beam. That is, the beam energy is increased. The hexapole electromagnet 14 excites resonance on the beam by applying a magnetic filed on the beam according to the supplied current. This resonance is used when the beam is made to emit from the synchrotron 1.

When the beam is accelerated up to an energy set by the control device 3 in the synchrotron 1, the control device 3 outputs the voltage command value to a power supply (not shown in the figure) of the high-frequency applying device 11. This power supply supplies a voltage whose value is entered to a high-frequency applying device 11. The high-frequency applying device 11 generates a high-frequency electric filed in proportion to the supplied voltage and applies the high-frequency electric field to the beam, and makes the beam emit from the synchrotron 1. Specifically, the high-frequency applying device 11 applies the high-frequency electric filed to the beam while a stability limit is kept constant. Through the application of the high-frequency electric field, the betatron vibrational amplitude increases and the beam that exceeds the stability limit resonates harmony with the magnetic field of the hexapole electromagnet 14 and is made to emit from the synchrotron 1. The beam emitted from the synchrotron 1 is guided to the rotational irradiation device 2.

The control device 3 outputs current command values to power supplies (not shown in the figure) of the deflecting electromagnet 21 and the quadruple electromagnet 22 during the beam is accelerated in the synchrotron 1. The power supplies supply currents whose values were entered to the deflecting electromagnet 21 and the quadruple electromagnet 22, respectively. The beam that is entered into the rotational irradiation device 2 is guided to the scanning electromagnets 23 and 24 along a track set beforehand by the deflecting electromagnet 21 and the quadruple electromagnet 22.

The control device 3 outputs the current command values to the power supplies of the deflecting electromagnet 211 and the quadruple electromagnet 22, and also outputs the position data of the irradiation areas A11, A12 . . . And the beam energy value to the scanning electromagnet control devices 25 and 26. The scanning electromagnet control devices 25 and 26 calculate the exciting current values for respective irradiation areas A11, A12 . . . that are necessary for scanning electromagnets 23 and 24 to apply the beam to respective irradiation areas A11, A12, . . . based on the entered position data of the irradiation areas A11, A12, . . . and the beam energy value. Furthermore, the scanning electromagnet control devices 25 and 26 calculate voltage values necessary for the scanning electromagnets 23 and 24 to apply the beam to respective irradiation areas A11, A12, . . . based on the exciting currents. Among the voltage values obtained, to start with, the voltage corresponding to A91 (a first irradiation area to be irradiated in the layered area L9) is outputted by the scanning electromagnet control devices 25 and 26 to the scanning electromagnet power supplies 27 and 28 as voltage command values. The scanning electromagnet power supplies 27 and 28 apply the voltages to the scanning electromagnets 23 and 24 based on the given voltage command values. In the scanning electromagnetic 23 and 24 flow the exciting currents according to the applied voltages, and the magnetic fields according to the exciting currents are generated. Then, by means of these magnetic fields, the scanning electromagnet 23 deflects the beam in an X-direction, and the scanning electromagnet 24 deflects the beam in an Y-direction, respectively. Details of the scanning electromagnet control devices 25 and 26 and the scanning electromagnet power supplies 27 and 28 will be described later.

Figure 4:
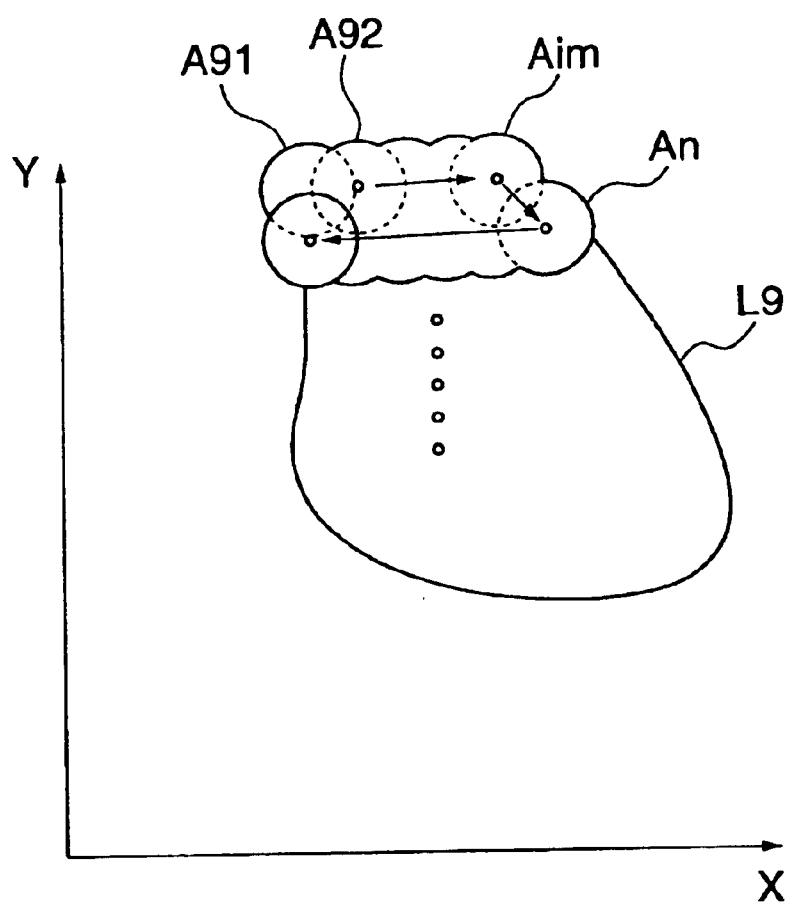
FIG. 4 is a diagram showing positions of the irradiation areas A91, A92, . . . in a layered area L9 of FIG. 3.

The beam deflected by the scanning electromagnets 23 and 24 is applied to the irradiation area A91 of the affected part after passing through a dose monitor 29. FIG. 4 shows a setting example of the irradiation areas in the layered area L9. In the present embodiment, the irradiation areas A91, A92 . . . , A9m, A9n, . . . are irradiated in order.

The dose monitor 29 measures the irradiation dose that is applied to the affected part. Actual measurement values of the beam irradiation dose by the dose monitor 29 are entered into the control device 3. The control device 3 compares the value of the irradiation does that was obtained beforehand (set value) and the entered actual measurement value, and outputs the emission stop command to the synchrotron 1 at a point of time when the actual measurement value reaches the set value. More specifically, the control device 3 outputs the emission stop command to the power supply of the high-frequency applying device 11 and thereby supply of the voltage to the high-frequency applying device 11 is stopped. Consequently, occurrence of the high-frequency electric field by the high-frequency applying device 11 is stopped, and the emission of the beam from the synchrotron 1 is also stopped. By the way, when the beam going around the synchrotron 1 disappears before the actual measurement value reaches the set value, an operator is simply requested to make the beam newly enter the synchrotron 1 from the preaccelerator 4 and accelerate it up to an energy set in the synchrotron 1, and make the beam emit again.

When the beam irradiation to the irradiation area A91 was finished in this way, next the beam is applied to the irradiation area A92. When the beam irradiation to the irradiation area A91 was finished, the control device 3 outputs the irradiation area change command to the scanning electromagnet control devices 25 and 26. The scanning electromagnet control devices 25 and 26 into which the irradiation area change commands are entered outputs the voltage command values indicating voltage values for the irradiation area A92 to the scanning electromagnet power supplies 27 and 28. The scanning electromagnet power supplies 27 and 28 apply voltages to the scanning electromagnets 23 and 24, respectively, according to the voltage command values, and the exciting currents in proportion to the applied voltages flow in the scanning electromagnets 23 and 24, respectively. Then, the magnetic fields in proportion to these exciting currents are generated in the scanning electromagnets 23 and 24. When the voltages to be applied to the scanning electromagnets 23 and 24 are changed, the high-frequency applying device 11 applies the high-frequency electric field to the beam again and makes the beam emit from the synchrotron 1. The beam emitted from the synchrotron 1 is deflected by the scanning electromagnets 23 and 24, and then applied to the irradiation area A92. By the way, in the present embodiment, the irradiation area A92 is out of the alignment from the irradiation area A91 in a X-direction, as shown in FIG. 4, but is not out of alignment in the Y-direction, and therefore the exciting current flowing in the scanning electromagnet 24 is kept unchanged for both cases: when the irradiation area A91 is irradiated, and when the irradiation area A92 is irradiated. That is, when the irradiation position of the beam is changed over, from the irradiation area A91 to the irradiation area A92, only the exciting current flowing in the scanning electromagnet 23 is changed. By the way, as is the case where the beam is applied to the irradiation area A91, also when the beam is applied to the irradiation area A92, the actual measurement value by the dose monitor 29 and the set value stored in the control device 3 are compared and at a point of time when the actual measurement value reaches the set value, the emission of the beam from the synchrotron 1 is stopped.

By repeating such procedures, the beam is applied to the each irradiation areas A91, A92, . . . of the layered area L9 so that the beam of the irradiation dose set for each irradiation is applied. By the way, when the beam irradiation position is changed over, from the irradiation area A91 to the irradiation area A92, the exciting current flowing in the scanning electromagnet 24 are not changed; when the irradiation position of the beam is changed also in the Y-direction as is the case where the beam irradiation position is changed, from the irradiation area A9m to the irradiation area A9n, the exciting current flowing in the scanning electromagnet 24 is also changed.

When all the irradiation areas in the layered area L9 have been irradiated with the beam, next each of irradiation areas in the layered area L8 is irradiated with the beam. The procedure by which the layered area L8 is irradiated with the beam is similar to that of the case of the layered area L9, although the beam energy is different. The control device 3 controls the synchrotron 1 and the rotational irradiation device 2 so that the beam is applied to the layered area L8. Subsequently the similar procedure is repeated up to the layered area L1 and thus the entire affected part is irradiated with the beam.

Figures 5A, 5B:
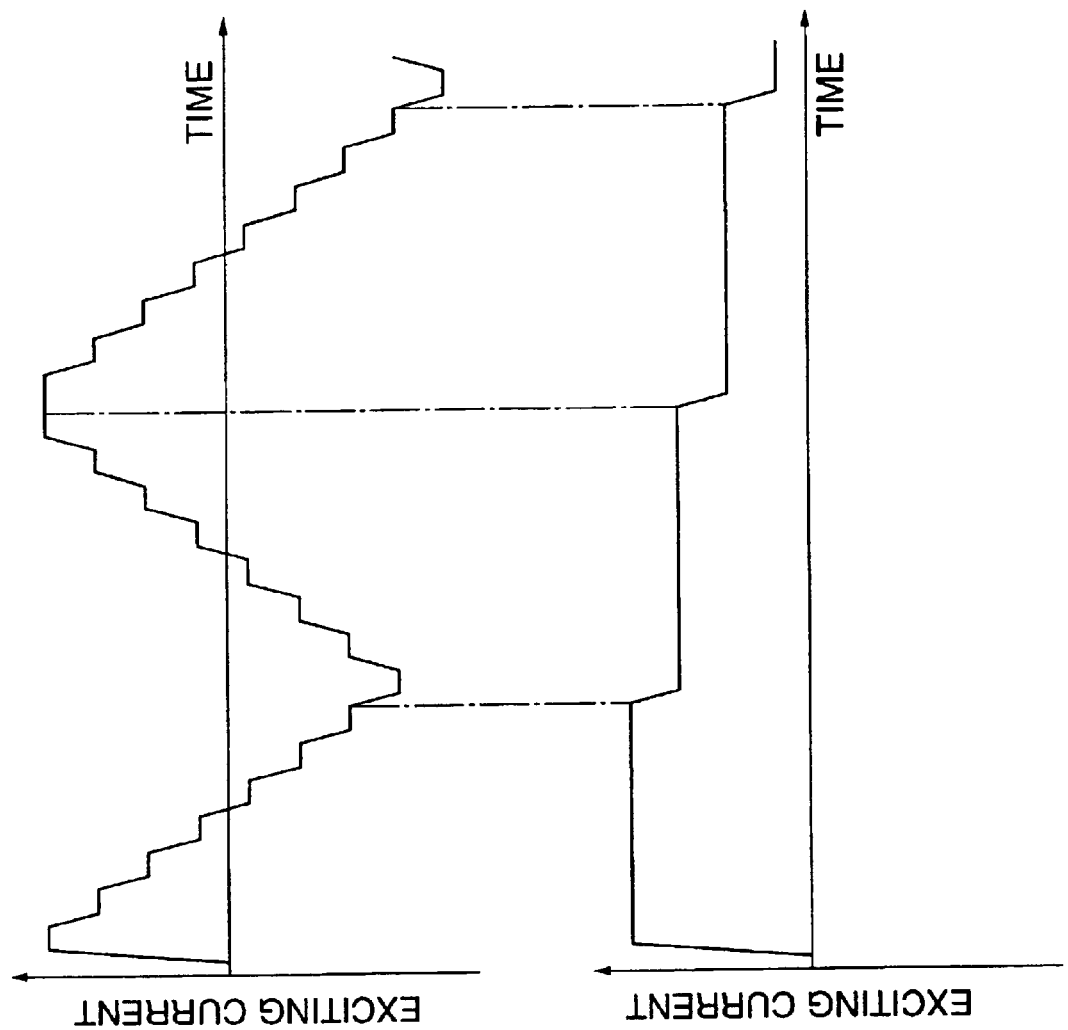
FIG. 5 is a graph showing waveforms of the exciting currents flowing in the scanning electromagnets 23 and 24 of FIG. 2.

In case the beam is applied to each of irradiation areas in such a way that the irradiation areas in the affected part are set as shown in FIG. 4, the exciting currents that are necessary at the scanning electromagnet 23 for deflecting the beam in the X-direction and at the scanning electromagnet 24 for deflecting the beam in the Y-direction are as shown in FIGS. 5(a) and (b), respectively. In the FIG. 5, when the exciting current is kept unchanged to the time, the magnetic field generated by the scanning magnet is also unchanged, and therefore the beam irradiation position is controlled to be fixed; when the exciting current is being changed to the time, the magnetic field generated is also being changed, and therefore the beam irradiation position is being moved. As shown in FIG. 5, in the present embodiment, the beam is scanned only in the X-direction to perform the beam irradiation for each irradiation area by decreasing the exciting current of the scanning electromagnet 23 for deflecting the beam in the X-direction stepwise while the exciting current of the scanning electromagnet 24 for deflecting the beam in the Y-direction is kept constant. Then, when the irradiation in the X-direction was completed from end to end (that is, in the example of FIG. 4, from the irradiation area A91 to the irradiation area A9m), the beam is shifted in the Y-direction by decreasing the exciting current of the scanning electromagnet 24 and the beam is scanned in the X-direction reversely by increasing the exciting current of the scanning electromagnet 23 stepwise. By repeating this procedure, the beam is scanned to irradiate the entire affected apart.

Next, referring to FIG. 1, operations of the scanning electromagnet control device 25 and the scanning electromagnet power supply 27 will be described in detail. By the way, the scanning electromagnet control device 26 and scanning electromagnet power supply 28 has a similar configuration; therefore its explanation is omitted.

As shown in FIG. 1, the scanning electromagnet power supply 27 has two power supply units 27a and 27b both of which are different in that while the power supply unit 27b has a DC filter 277 at the output side, the power supply unit 27a has no DC filter. Thus, since the power supply unit 27a has no DC filter, the voltage outputted by the power supply unit 27a does not suffer the time delay in its outputted voltage. Consequently, in the present embodiment, the exciting current flowing in the scanning electromagnet 23 is changed in a short time by means of a voltage outputted by the power supply unit 27a, and the exciting current after being changed is controlled to be constant by the power supply unit 27b. That is, the power supply unit 27a and power supply unit 27b take partial functions, a function of changing the exciting current in a short time (changing over an irradiation area) and a function of keeping the exciting current constant (keeping the beam irradiation position in an irradiation area), respectively.

In the FIG. 1, each position data of the irradiation area is entered into the scanning electromagnet control device 25 from the control device 3, as described above. The scanning electromagnet control device 25 calculates the voltage command values Va and Vb which are indicated to respective power supply units 27a and 27b based on the entered position data.

First, the method of finding the voltage command value Va to the power supply unit 27a will be described. The scanning electromagnet control unit 25 calculates the exciting currents, for each irradiation area, which is necessary for the scanning electromagnet 23 to position the beam at each irradiation area from the entered position data and beam energy value. Next, between the adjacent areas whose turns of the beam irradiation area of sequential turns, the difference of the obtained exciting currents, namely the variation of the exciting current ΔI is computed. For example, suppose that the exciting current necessary for the scanning electromagnet 23 to put the beam irradiation position to the irradiation area A91 is denoted by I91 and the exciting current necessary for the scanning electromagnet 23 to put the beam irradiation position to the irradiation area A92, where the beam is applied next to the irradiation area A91, is denoted by I92, the difference of the both exciting currents is expressed by ΔI=I92−I91. In other words, this ΔI is the amount of change of the exciting current that is required to change over the irradiation area.

Here, regarding the voltage V applied to the scanning electromagnet 23 and the amount of change of the exciting current ΔI in the scanning electromagnet 23, the relation of Equation 1 stands, $$V = L \cdot \Delta I / t \tag{Equation 1}$$

where L denotes the inductance of the scanning electromagnet 23, t the time necessary for the exciting current to be changed by ΔI. In Equation 1, since the inductance L is an intrinsic value in the scanning electromagnet 23, namely a constant, the voltage V can be found using the calculated ΔI by giving the time t to the scanning electromagnet control device 25 beforehand. This voltage V is a voltage value that is necessary for the exciting current of the scanning electromagnet 23 to be changed by ΔI in time t, namely a voltage value necessary for the irradiation area to be changed over. Therefore, the scanning electromagnet control device 25 finds the voltage value V for each irradiation area based on Equation 1 and stores the each voltage value V thus obtained in memory of the scanning electromagnet control device 25 as a voltage command value Va to be given to the power supply unit 27a.

Time t is a time necessary for the exciting current of the scanning electromagnet 23 to be changed by I, that is, a time necessary for the irradiation area to be changed over, a short time as small as possible should be set in order to shorten the treatment time. However, if too short time is set, the voltage command value Va becomes too large, accordingly loads of the power supply unit 27a for generating the voltage and the scanning electromagnet 23 where the voltage is applied inevitably increase. Therefore, the operator sets an appropriate value inconsideration of a balance between these loads and the treatment time.

Next, the method of finding the voltage command value Vb to be given to the power supply unit 27b will be described. As described above, the power supply unit 27b is a circuit for controlling the exciting current to be constant, namely for applying a voltage for keeping the beam irradiation position in the irradiation area to the scanning electromagnet 23. Therefore, for a voltage command value Vb to be given to the power supply unit 27b, it is simply sufficient to find a voltage value that is used to make the exciting current, which is necessary for the beam irradiation position to be set in each irradiation area, flow in the scanning electromagnet 23. Denoting the necessary exciting current by I and the resistance of the scanning electromagnet 23 by R, this voltage value can be obtained with Equation 2, $$V = R \cdot I \tag{Equation 2}$$

The voltage value V can be calculated using Equation 2 for each irradiation area because the exciting current I necessary for the beam irradiation position to be set in each irradiation area was obtained for each irradiation area based on the position data and beam energy value which were entered from the control device 3 in the scanning electromagnet control device 25, and the resistance R of the scanning electromagnet 23 is a constant. Each voltage value V thus obtained is stored in the memory of the scanning electromagnet control device 25 for each irradiation area as the voltage value necessary for the beam irradiation position to be set in each irradiation area, namely a voltage command value Vb to be given to the power supply unit 27b.

When the beam is applied to the affected part, the scanning electromagnet control device 25 outputs the voltage command value Va for moving the beam irradiation position to the irradiation area A91 and the voltage command value Vb for keeping the beam irradiation position in the irradiation area A91, among the voltage command values Va and Vb stored in the memory, to power supply units 27a and 27b, respectively.

In the power supply unit 27a, the voltage command value Va given by the scanning electromagnet control device 25 is entered into an AC-DC converter 272a. Further, an AC voltage is supplied to the AC-DC converter 272a from a source power supply via a transformer 271. The AC-DC converter 272a converts the supplied AC voltage into a DC voltage of the voltage command value Va. The DC voltage obtained by the AC-DC converter 272a is applied to an input port of the inverter 273a via a smoothing capacitor.

To the gate driver 274a of the power supply unit 27a, the voltage command value Va is outputted to the AC-DC converter 272a and at the same time an ON signal is given by the scanning electromagnet control device 25. The gate driver 274a makes the inverter 273a output a DC voltage by controlling a switching element of the inverter 273a while the ON signal is being given by the scanning electromagnet control device 25. By the way, the DC voltage value outputted by the inverter 273a equals a voltage value applied to the input port of the inverter 273a, namely the voltage command value Va outputted by the scanning electromagnet control device 25.

The outputted voltage of the inverter 273a is applied to the scanning electromagnet 23 as an output voltage of the power supply unit 27a, and the exciting current flows in the scanning electromagnet 23 to which the voltage was applied.

Further, the scanning electromagnet control device 25 outputs the voltage command value Va to the power supply unit 27a, and at the same time outputs the voltage command value Vb to the power supply unit 27b. In the power supply unit 27b, the voltage command value Vb given by the scanning electromagnet control device 25 is entered into a control unit 275. The control unit 275 controls a PWM control unit 276 based on the entered voltage command value Vb, and controlling the AC-DC converter 272b, converts the AC voltage, which is entered into the AC-DC converter 272b from the source power supply via the transformer 271, into a DC voltage. The DC voltage obtained by the AC-DC converter 272b is applied to the input port of the inverter 273b via a smoothing capacitor.

The PWM control unit 276 outputs ON signals and OFF signals repeatedly to the gate driver 274b, and the gate driver 274b controls ON and OFF of the switching element of the inverter 273b in response to ON signals and OFF signals entered. The inverter 273b outputs a DC voltage by the ON-and-OFF control of the switching element. By the way, the inverter 273b is PWM controlled so that this output voltage value equals the voltage command value Vb.

The DC voltage outputted by the inverter 273b is applied to the scanning electromagnet 23 after its pulsating component is removed by the DC filter 277, but it takes some time for the voltage value of the output port of the DC filter 277 to reach Vb because the filter 277 has a delay element.

The scanning electromagnet control device 25 counts elapsed time after outputting the ON signal to the gate driver 274a of the power supply unit 27a, and at a point of time when the counted time reaches the time t set by the operator beforehand, the scanning electromagnet control device 25 stops the output of the ON signal to the gate driver 274a. When the input of the ON signal is stopped, the gate driver 274a controls the switching element of the inverter 273a so that the inverter 273a is made to be in a short-circuit condition. Thereby, the application of the voltage to the scanning electromagnet 23 by the inverter 273a of the power supply unit 27a is stopped. By the way, the voltage value Va is a voltage value necessary for the exciting current of the scanning electromagnet 23 to be changed by ΔI in time t, as described above, and by applying the voltage Va in time t, the exciting current of the scanning electromagnet 23 is changed by ΔI. That is, the exciting current changes to one necessary for the beam irradiation position to be moved in the irradiation area A91.

In this way, at a point of time when the application of the voltage to the scanning electromagnet 23 by the power supply unit 27a is stopped, the voltage value outputted by the DC filter 277 of the power supply unit 27b equals Vb, and hence the exciting current flowing in the scanning electromagnet 23 becomes an exciting current necessary for the beam irradiation position to be kept in the irradiation area A91, by the voltage of the voltage value Vb applied by the power supply unit 27b.

In this way, the exciting current necessary for the beam irradiation position to be kept in the irradiation area A91 flows in the scanning electromagnet 23, and thereby the beam is applied to the irradiation area A91 of the affected part. Subsequently, when the beam of a set irradiation dose has been applied to the irradiation area A91, the control device 3 outputs the irradiation area change command to the scanning electromagnet control device 25. The scanning electromagnet control device 25, to which the irradiation change command is entered, outputs the voltage command value Va for moving the beam irradiation position to the irradiation area A92 and the voltage instruction command value Vb for keeping the beam irradiation position in the irradiation area A92, among the voltage command values Va and Vb stored in the memory, to respective power supply units 27a and 27b. Operations of the scanning electromagnet control device 25 and the scanning electromagnet power supply 27 after that stage are similar to those of the case of the irradiation area A91.

In the foregoing, described are the operations of the scanning electromagnet control device 25 and the scanning electromagnet power supply 27. The scanning electromagnet control device 26 and the scanning electromagnet power supply 28 also operate in the same manner. Through these operations, the beam is applied to the affected part while the irradiation area where the beam is applied is being changed over.

Figures 6A, 6B:
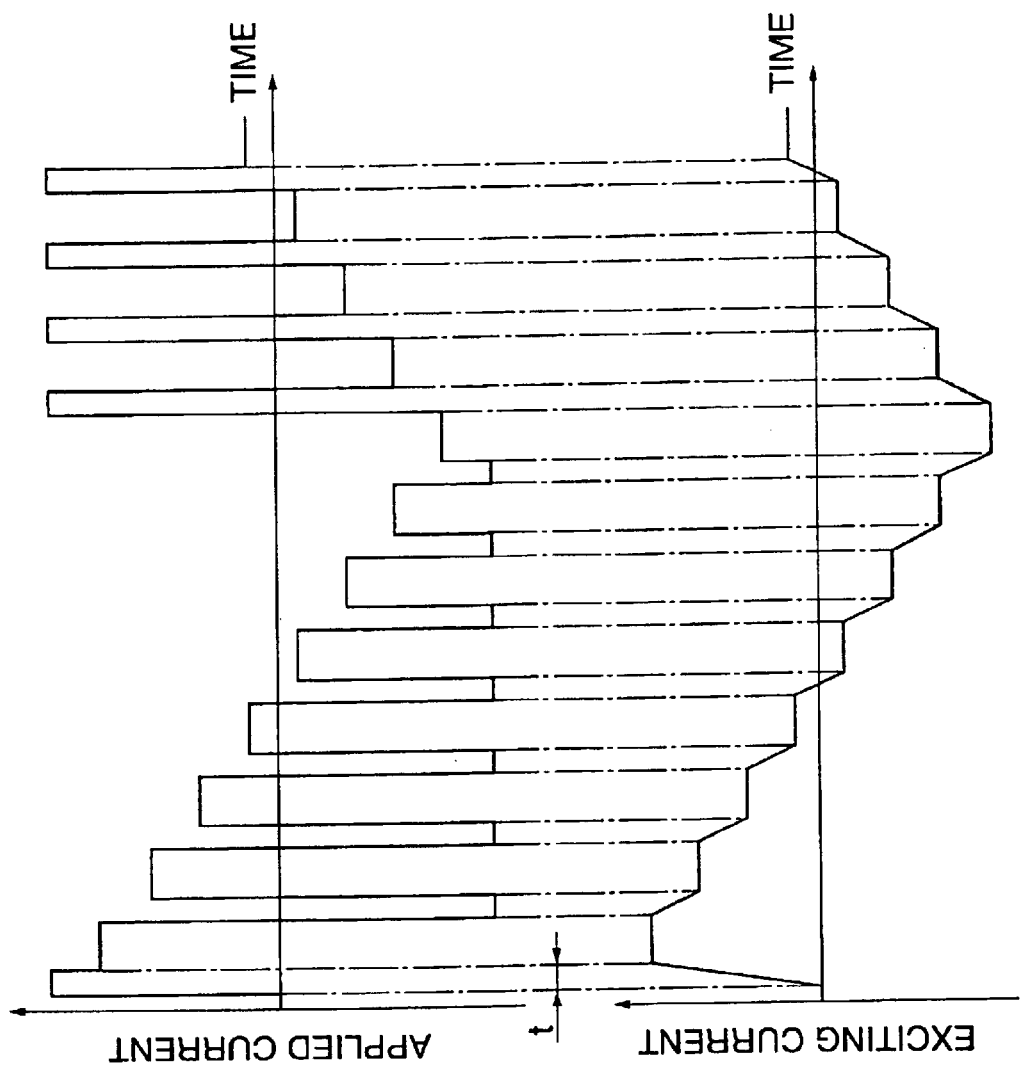
FIG. 6 is a graph showing a waveform of the voltage applied to the scanning electromagnet 23 of FIG. 2 and a waveform of the current flowing in the scanning electromagnet 23 by the voltage.

FIG. 6 shows the relationship between the applied voltage which is applied to the scanning electromagnet 23 by the scanning electromagnet power supply 27 and the exciting current flowing in the scanning electromagnet 23 by means of the applied voltage. By the way, the scanning electromagnet power supply 28 and the scanning electromagnet 24 exhibit the similar relationship. As shown in FIG. 6(a), to begin with, a large positive voltage is applied to the scanning electromagnet 23 in time t. This voltage is a voltage outputted by the power supply unit 27a, namely the voltage of the voltage value Va. Due to the application of this voltage, the exciting current flowing in the scanning electromagnet 23 increases by the amount of variation according to the voltage value of the applied voltage in time t, as shown in FIG. 6(b). After that, at the point of time when the time t elapsed after the application of the voltage by the power supply unit 27a was started, the application of the voltage by the power supply unit 27a is stopped and the applied voltage to be applied to the scanning electromagnet 23 becomes the voltage of the voltage value Vb outputted by the power supply unit 27b. By virtue of this, the exciting current flowing in the scanning electromagnet 23 is controlled to be constant, as shown in FIG. 6(b).

In this way, the exciting current is changed to the required value in time t by means of the large voltage applied by the power supply unit 27a, the application of the voltage by the power supply unit 27a is stopped at a point of time when the time t elapsed, and the exciting current is controlled to be a required constant value by means of the application of the voltage by the power supply unit 27b. That is, the beam irradiation position is moved to an irradiation area where the beam is to be applied in time t by means of the voltage applied by the power supply unit 27a, and subsequently the beam irradiation position is kept in the irradiation area where the beam is to be applied by means of the voltage applied by the power supply unit 27b. Hereinafter, the voltage outputted by the power supply unit 27a is called a forced voltage and the voltage outputted by the power supply unit 27b is called a fixed voltage. By the way, it can be said that if the exciting current flowing in the scanning electromagnet 23 is desired to be increased, a positive forced voltage is applied; if the exciting current is desired to be decreased, a negative forced voltage is applied, as shown in FIG. 6. As described above, by using the forced voltage and the fixed voltage in combination, the exciting current is controlled stepwise as shown in FIG. 6(b).

As described in the foregoing, since in the present embodiment the scanning electromagnet power supply 27 has a power supply unit 27a having no filter and a power supply unit 27b having a DC filter 277, when the beam irradiation position is changed over, the power supply unit 27a free from a delay element is used to apply the forced voltage to the scanning electromagnet 23 and thereby the exciting current can be changed in a short time. Therefore, the irradiation area where the beam is applied can be changed over in a short time, hence reducing the treatment time. On the other hand, when the beam irradiation position is maintained, the exciting current can be kept constant by applying the voltage, whose pulsating component is removed by the power supply unit 27b having the DC filter, to the scanning electromagnet 23. Therefore, the beam irradiation position can be prevented from being moved out of the irradiation area, so that the beam can be applied uniformly to the affected part. Thus, according to the present embodiment, the beam can be applied uniformly to the affected part and the treatment time can be curtailed.

BY the way, in the present embodiment, the irradiation of the beam is stopped when the irradiation area where the beam is applied is changed over. However, when the time required to change over the irradiation area can be sufficiently shortened compared to the time when the beam is applied to the irradiation area, the irradiation of the beam may not be stopped when the irradiation area is changed over. This is because that when the time required to change over the irradiation area is sufficiently short, the beam irradiation dose irradiated in the period of time when the irradiation area is changed over can be ignored.

In the present embodiment described above, time t that is required to change over the irradiation area is given as a constant value; therefore in case the each interval of the irradiation areas is constant, namely the variation of the exciting current $\Delta I$ is a constant, the absolute value of the forced voltage value Va is also a constant. Consequently, in that case, the forced voltage value Va is not necessarily calculated each time the irradiation area is changed over, but it is only necessary to set the sign of positive or negative. By the way, the time t required to change over the irradiation area is not necessarily a constant, but may be set to a different value according to the situation. Moreover, in the present embodiment, a scheme was taken where the forced voltage value is found with the use of the time t set beforehand. However the forced voltage may be set as a constant value beforehand. In that case, the time t is determined by the forced voltage value Va and the interval between each irradiation area.

Further, in the present embodiment, a scanning schema is employed where the beam is scanned with the two scanning electromagnets 23 and 24. However, in stead of the scanning of the beam by the scanning electromagnets, a bed on which a patient is supported may be moved. For example, in stead of the employment of the scanning electromagnet 24 for scanning the beam in the Y-direction, a bed movable in the Y-direction may be used. Even in that case, the present invention is still effective to the scanning electromagnet 23 for scanning the beam in the X-direction.

Further, in the present embodiment, as shown in FIG. 4, a scanning scheme is employed where the beam is scanned in the X-direction while the beam is fixed in the Y-direction and after the scanning in the X-direction is finished, the beam is scanned in the Y-direction, and subsequently the beam is scanned again in the X-direction. However, the present invention is not limited within this scanning scheme and but the present invention is also effective with any scanning scheme where the affected part is divided into a plurality of irradiation areas and each irradiation area is irradiated with the beam one by one, such as scanning scheme where circles are drawn, and a scanning scheme where the beam is scanned in the X-direction and in the Y-direction simultaneously, such as a zigzag scanning.

If voltage detectors for detecting the voltage applied to the scanning electromagnets 23 and 24 and current detectors for detecting exciting currents flowing in the scanning electromagnets 23 and 24 are added to the present embodiment and a display unit for displaying waveforms of currents and voltages detected by the voltage detector and the current detector is employed, it can be checked whether the voltage applied to the scanning electromagnets 23 and 24 as well as the exciting current flowing in the scanning electromagnets 23 and 24 are in desired waveforms can be verified.

Furthermore, in the present embodiment, described is the charged particle beam irradiation equipment for applying the beam to the affected part of a cancer patient. However, irradiation objects cannot be limited within the affected part of a cancer patient, but the present invention can also be applied to the charged particle beam irradiation equipment for scanning the beam to irradiate semiconductors, seeds of plants, etc.

Embodiment 2

Figure 7:
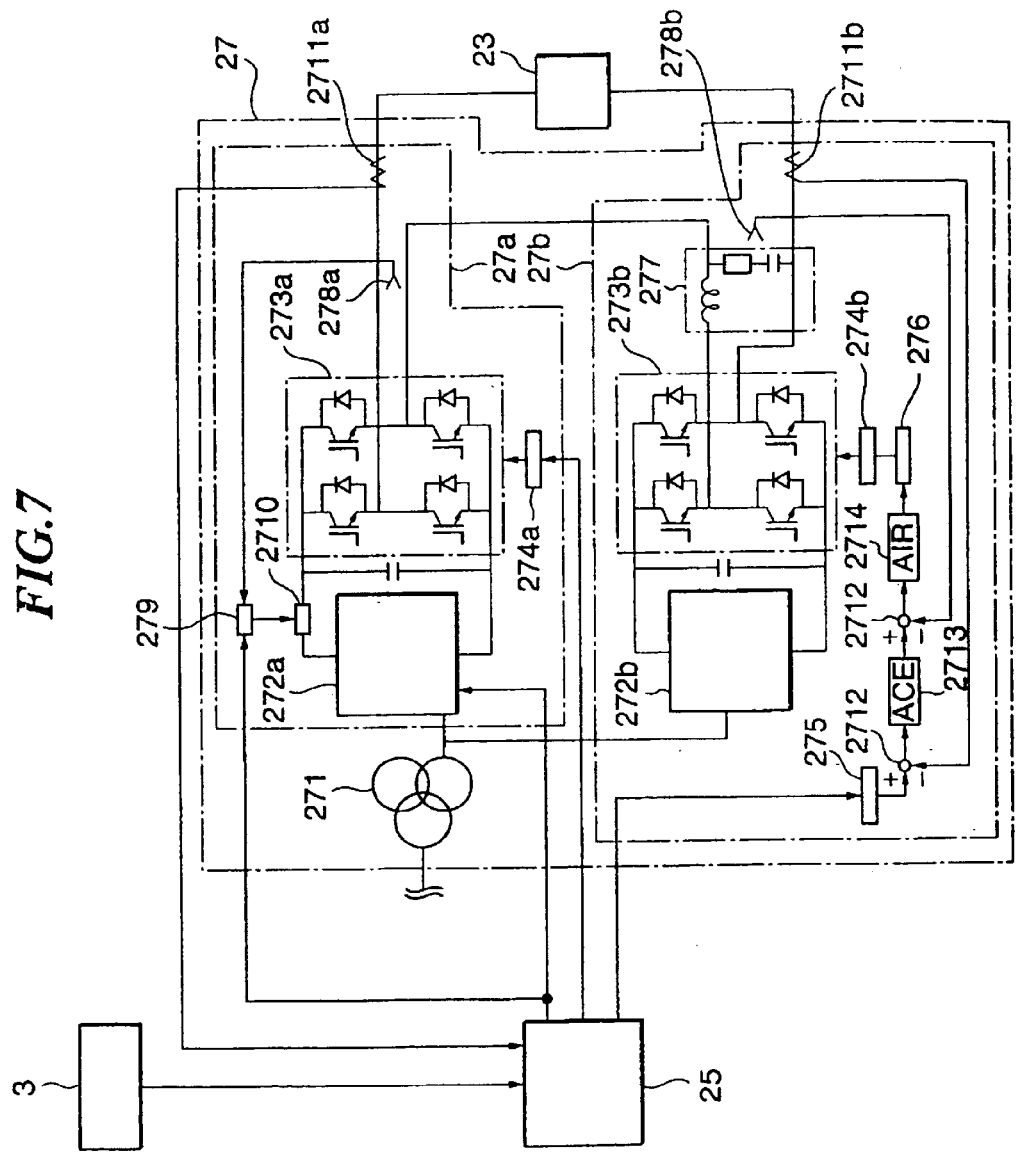
FIG. 7 is a block diagram of the scanning electromagnet power supply in the charged particle beam irradiation equipment that is another embodiment according to the present invention.

Referring to FIG. 7, the charged particle beam irradiation equipment, namely another embodiment of the present invention, will be described. The charged particle beam irradiation equipment according to this embodiment is different from the Embodiment 1 mainly in the configuration of the scanning electromagnet power supply. In the following described is different points from Embodiment 1.

FIG. 7 shows a configuration of a scanning electromagnet power supply 27 according to the present embodiment. By the way, a scanning electromagnet power supply 28 has a similar configuration; therefore its explanation is omitted. Further, a total block diagram of the present embodiment is the same as Embodiment 1, as in FIG. 2.

In the FIG. 7, the power supply unit 27a has a voltage detector 278a, and the voltage detector 278a detects the output voltage of the inverter 273a, namely the output voltage of the power supply unit 27a. A voltage detected value detected by the voltage detector 278a is entered into a comparator 279. The voltage command value Va is also entered into the comparator 279 from the scanning electromagnet control device 25, and the comparator 279 subtract the voltage detected value from the voltage command value to compute a voltage deviation. Further, the comparator 279 controls a chopper 2710 based on the obtained voltage deviation so that the output voltage of the inverter 273a equals the voltage command value Va. By virtue of this control, the control accuracy of the voltage outputted by the inverter 273a is increased.

In FIG. 7, the power supply unit 27a has a current detector 2711a for detecting the exciting current flowing in the scanning electromagnet 23, and the current detector 2711a outputs the current detected value detected thereby to the scanning electromagnet control device 25. The scanning electromagnet controls device 25 compares the exciting current value necessary for the beam irradiation position to be set in the irradiation area, which was obtained beforehand, and the current detected value that is entered, and when the both current values coincides with each other, an ON signal that is being outputted to the gate driver 274a of the power supply unit 27a is stopped. In other words, in the present embodiment, at a point of time when the value of the exciting current flowing in the scanning electromagnet 23 reaches the exciting current value necessary for the beam irradiation position to be set in the irradiation area where the beam is applied, the forced voltage that is being outputted by the power supply unit 27a is stopped. Owing to this scheme, in the present embodiment, the counting of time in the scanning electromagnet control device 25, which is requisite in Embodiment 1, becomes unnecessary.

In FIG. 7, the power supply unit 27b comprises a current detector 2711b for detecting the component of variation in the output current and a voltage detector 278b for detecting the component of variation in the output voltage, and can improve further the control accuracy of the currents and voltages that are outputted, by feedbacking the signals detected by respective detectors using an adder 2712 and also controlling both the current with a constant current control circuit (ACR) 2713 and the voltage with a constant voltage control circuit (AVR) 2714.

Other points except the points described above are similar to those of the Embodiment 1 and functions and effects that can be attained are similar to those.

In the Embodiments 1 and 2, the voltage values outputted by the power supply unit 27a are controlled by the AC-DC converter 272a. However, the output voltage value of the power supply unit 27a may be controlled by PWM controlling the inverter 273a. In such a case, control units whose configuration are similar to those of the control unit 275 and the PWG control unit 276 of the power supply unit 27b may be added to the power supply unit 27a.

Moreover, in Embodiments 1 and 2, accelerators other than synchrotron, for example a cyclotron and a LINAC, may be used as an accelerator for accelerating the charged particle beam. In addition, the method of the beam emission from the synchrotron is not limited to the method used in the Embodiments 1 and 2.

Moreover, in Embodiments 1 and 2, the rotational irradiation device 2 is used as the irradiation device. However, a fixed irradiation device may be used instead.

By the way, the voltage command value Vb that is given to the power supply unit 27b may be substituted with the current command value.

Industrial Applicability

The present invention can be applied to the charged particle beam irradiation equipment for applying a charged particle beam to an irradiation object such as the affected part of a cancer patient. Through the application of the present invention, the irradiation dose to the irradiation object can be made uniform and the irradiation time necessary for the charged particle beam to be applied to the irradiation object can be reduced.

What is claimed is:

1. A charged particle beam irradiation equipment for irradiating charged particle beam to an object, comprising a first scanning electromagnet for scanning a charged particle beam in a first direction, a second scanning electromagnet for scanning a charged particle beam in a second direction which intersecting with the first direction, a first power supply for applying a voltage to the first scanning electromagnet, and a second power supply for applying a voltage to the second scanning electromagnet, wherein said first power supply comprises a first power supply unit having no filter and a second power supply unit having a filter, said second power supply comprises another first power supply unit having no filter and another second power supply unit having another filter, a first scanning electromagnet control device for controlling said first power supply unit and said second power supply unit in said first power supply, and a second scanning electromagnet control device for controlling said another first power supply unit and said another second power supply unit in said second power supply.

2. A charged particle beam irradiation equipment according to claim 1, wherein said first scanning electromagnet control device controls said first power supply unit to output a voltage from said first power supply unit during a period when irradiation position of said charged particle beam irradiation is changed from a first irradiation position of said charged particle beam irradiation is changed from a first irradiation area to a second irradiation area in the irradiation object in said first direction, and controls said second power supply unit to output a voltage from said second power supply unit during a period when said second irradiation area is irradiated with said charged particle beam, and said second scanning electromagnet control device controls said another first power supply unit to output a voltage from said another first power supply unit during a period when irradiation position of said charged particle beam irradiation is changed from a third irradiation area to a fourth irradiation area in the irradiation object in said second direction, and controls said another second power supply unit to output a voltage from said another second power supply unit during a period when said fourth irradiation area is irradiated with said charged particle beam.

3. A charged particle beam irradiation equipment according to claim 1, wherein said first power supply unit in said first power supply comprises a first inverter to output a DC as said voltage, said second power supply unit in said first power supply comprises a second inverter to output a DC as said voltage to said filter, said another first power supply unit in said second power supply comprises another said first inverter to output a DC as said voltage, and said another second power supply unit in said second power supply comprises another said second inverter to output a DC as said voltage to said another filter.

4. A charged particle beam irradiation equipment according to claim 3, wherein said first scanning electromagnet control device controls said first inverter to output a DC from said first inverter during a period when irradiation position of said charged particle beam irradiation is changed from a first irradiation area to a second irradiation area in the irradiation object in said first direction, and controls said second inverter to output a DC from said second inverter during a period when said second irradiation area is irradiated with said charged particle beam, and said second scanning electromagnet control device controls said another first inverter to output a DC from said another first inverter during a period when irradiation position of said charged particle beam irradiation is changed from a third irradiation area to a fourth irradiation area in the irradiation object in said second direction, and controls said another second inverter to output a DC from said another second inverter during a period when said fourth irradiation area is irradiated with said charged particle beam.

5. A charged particle beam irradiation equipment according to claim 3, wherein said first power supply comprises:

a first control device for controlling an output of DC from said first inverter in said first power supply, and a second control device for controlling an output of DC from said second inverter in said first power supply;

said second power supply comprises:

a third control device for controlling an output of DC from said another first inverter in said second power supply, and a fourth control device for controlling an output of DC from said another second inverter in said second power supply; further wherein said first scanning electromagnet control device outputs a first control instruction for outputting a DC voltage from said first inverter in said first power supply to said first control device, and a second control instruction for outputting a DC voltage from said second inverter in said second power supply to said second control device; and said second scanning electromagnet control device outputs a third control instruction for outputting a DC voltage from said another first inverter in said second power supply to said third control device, and a fourth control instruction for outputting a DC voltage from said another second inverter in said second power supply to said fourth control device.

6. A charged particle beam irradiation equipment according to claim 5, wherein said second control device controls said second inverter in said first power supply with PWM control, and said fourth control device controls said another second inverter in said second power supply with PWM control.

7. A charged particle beam irradiation equipment according to claim 5, wherein said first scanning electromagnet control device outputs said first control instruction during a period when irradiation position of said charged particle beam irradiation is changed from a first irradiation area to a second irradiation area in the irradiation object in said first direction, and outputs said second control instruction during a period when said second irradiation area is irradiated with said charged particle beam, and said second scanning electromagnet outputs said third control instruction during a period when irradiation position of said charged particle beam irradiation is changed from a third irradiation area to a fourth irradiation area in the irradiation object in said second direction, and outputs said fourth control instruction during a period when said fourth irradiation area is irradiated with said charged particle beam.

8. A charged particle beam irradiation equipment according to claim 7, wherein said second control device controls said second inverter in said first power supply with PWM control, and said fourth control device controls said another second inverter in said second power supply with PWM control.

* * * * *